(12) United States Patent
Kubelik et al.

(10) Patent No.: US 9,778,224 B2
(45) Date of Patent: Oct. 3, 2017

(54) DIELECTRIC BARRIER DISCHARGE IONIZATION SOURCE FOR SPECTROMETRY

(71) Applicant: Smiths Detection Montreal Inc., Mississauga (CA)

(72) Inventors: Igor Kubelik, Mississauga (CA); Simon Feldberg, Vaughan (CA); Bohdan Atamanchuk, Mississauga (CA); Mark Piniarski, Mississauga (CA); Mark Lekhter, Toronto (CA); Daniel Levin, Woodbridge (CA); Vlad Sergeyev, Toronto (CA); Henryk Zaleski, Scarborough (CA)

(73) Assignee: Smiths Detection Montreal Inc., Missisauga, Ontario (CA)

( * ) Notice: Subject to any disclaimer, the term of this patent is extended or adjusted under 35 U.S.C. 154(b) by 0 days.

(21) Appl. No.: 15/039,586

(22) PCT Filed: Nov. 26, 2014

(86) PCT No.: PCT/CA2014/051126
§ 371 (c)(1),
(2) Date: May 26, 2016

(87) PCT Pub. No.: WO2015/077879
PCT Pub. Date: Jun. 4, 2015

(65) Prior Publication Data
US 2017/0023525 A1   Jan. 26, 2017

Related U.S. Application Data

(60) Provisional application No. 61/908,887, filed on Nov. 26, 2013.

(51) Int. Cl.
*G01N 27/68*   (2006.01)
*G01N 27/62*   (2006.01)

(52) U.S. Cl.
CPC .......... *G01N 27/68* (2013.01); *G01N 27/622* (2013.01)

(58) Field of Classification Search
USPC ..... 250/423 R, 423 F, 424, 288; 315/111.21, 315/111.81
See application file for complete search history.

(56) References Cited

U.S. PATENT DOCUMENTS

| 4,629,992 A * | 12/1986 | Nudelmont | G08B 17/11 324/439 |
| 6,414,702 B1 * | 7/2002 | Kubelik | B41J 2/415 315/111.81 |

(Continued)

FOREIGN PATENT DOCUMENTS

| CA | 2816116 A1 | 5/2012 |
| WO | 2008067395 A2 | 6/2008 |
| WO | 2012172436 A2 | 12/2012 |

OTHER PUBLICATIONS

International Search Report mailed Feb. 12, 2015 for PCT/CA2014/051126.

*Primary Examiner* — Bernard Souw
(74) *Attorney, Agent, or Firm* — Advent, LLP

(57) ABSTRACT

An ionization device includes a first electrode comprising a conductive member coated with a dielectric layer. The ionization device also includes a spine extending adjacent to and at least partially along the first electrode. The ionization device further includes a second electrode comprising conductive segments disposed adjacent the first electrode. Each one of the conductive segments contacts the spine at a respective contact location. The dielectric layer of the first electrode separates the conductive member of the first electrode from the spine and the second electrode. The ionization device is configured to create plasma generating (Continued)

locations corresponding to respective crossings of the first electrode and the second electrode.

20 Claims, 7 Drawing Sheets

(56) References Cited

U.S. PATENT DOCUMENTS

| | | | | |
|---|---|---|---|---|
| 6,703,784 | B2* | 3/2004 | Vonallmen | H01J 17/04 315/111.21 |
| 6,940,074 | B2* | 9/2005 | Hartley | H01J 3/027 250/286 |
| 7,993,489 | B2* | 8/2011 | Matsumoto | C23F 4/00 118/723 E |
| 8,173,959 | B1* | 5/2012 | Boumsellek | G01N 27/622 250/281 |
| 9,385,079 | B2* | 7/2016 | Chang | H01L 23/5256 |
| 2003/0230983 | A1* | 12/2003 | Vonallmen | H01J 17/04 315/111.21 |
| 2005/0121607 | A1* | 6/2005 | Miller | G01N 27/624 250/287 |
| 2006/0284102 | A1* | 12/2006 | Blanchard | H01J 49/0018 250/423 F |
| 2011/0121735 | A1* | 5/2011 | Penny | A61B 18/042 315/111.21 |
| 2015/0301427 | A1* | 10/2015 | Galstian | G02F 1/29 349/77 |

* cited by examiner

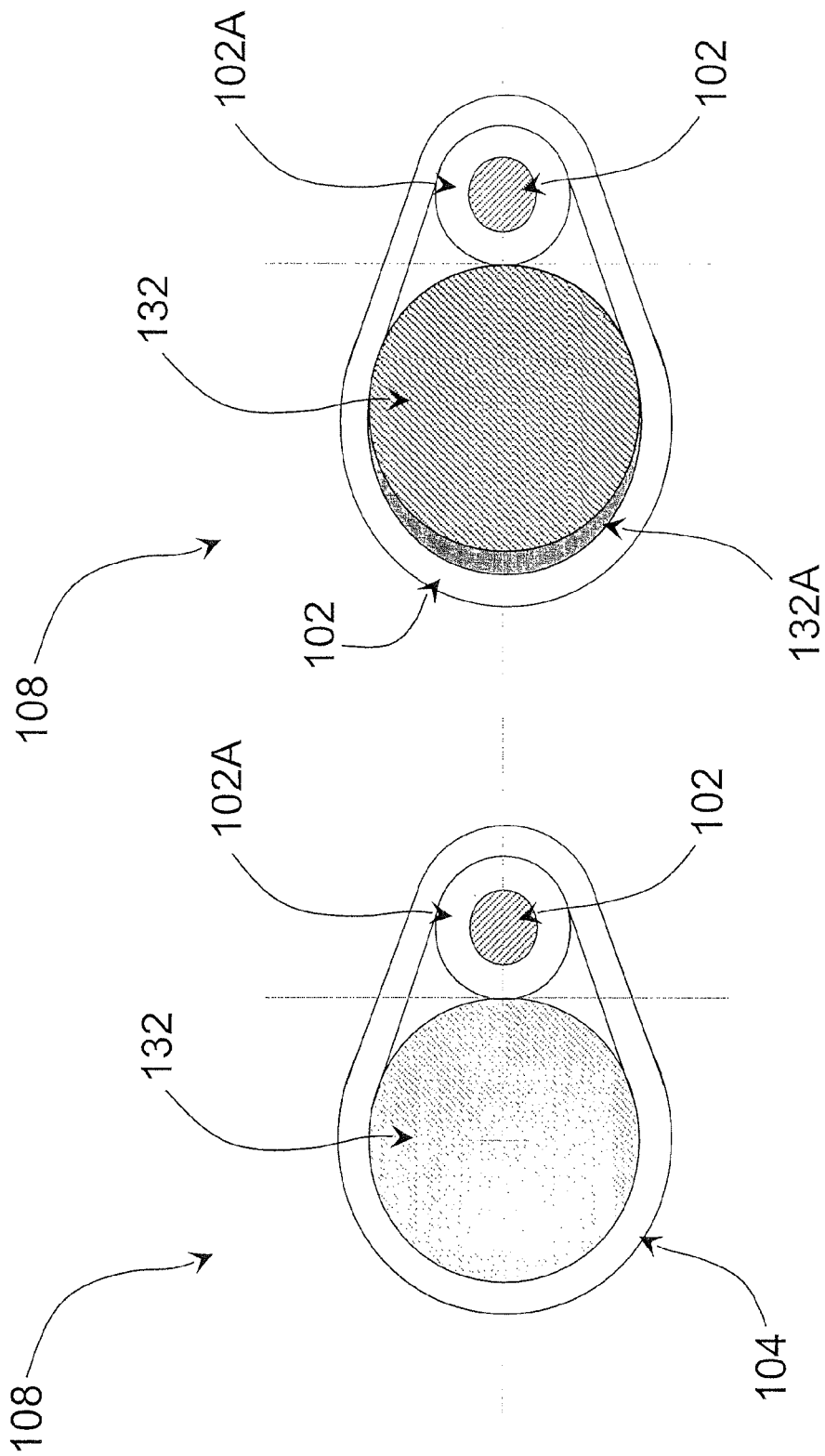

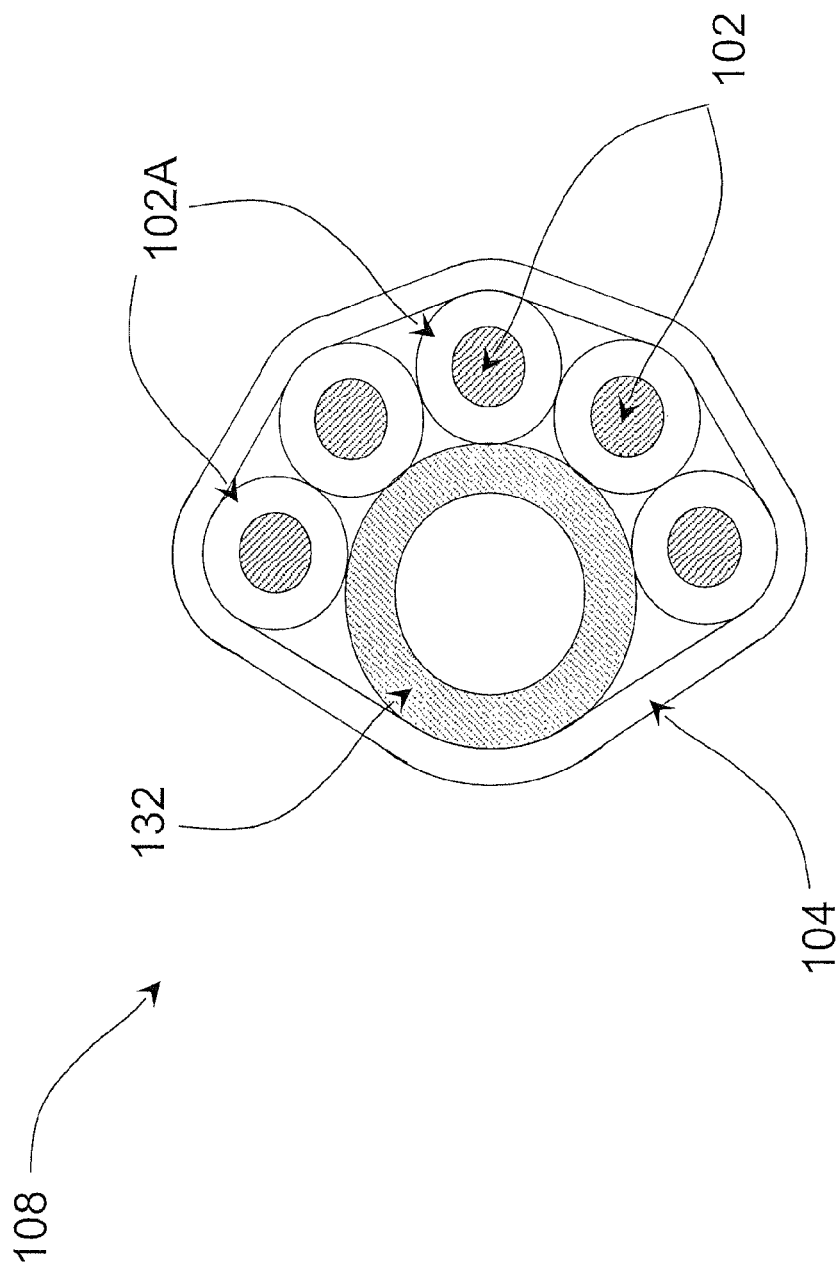

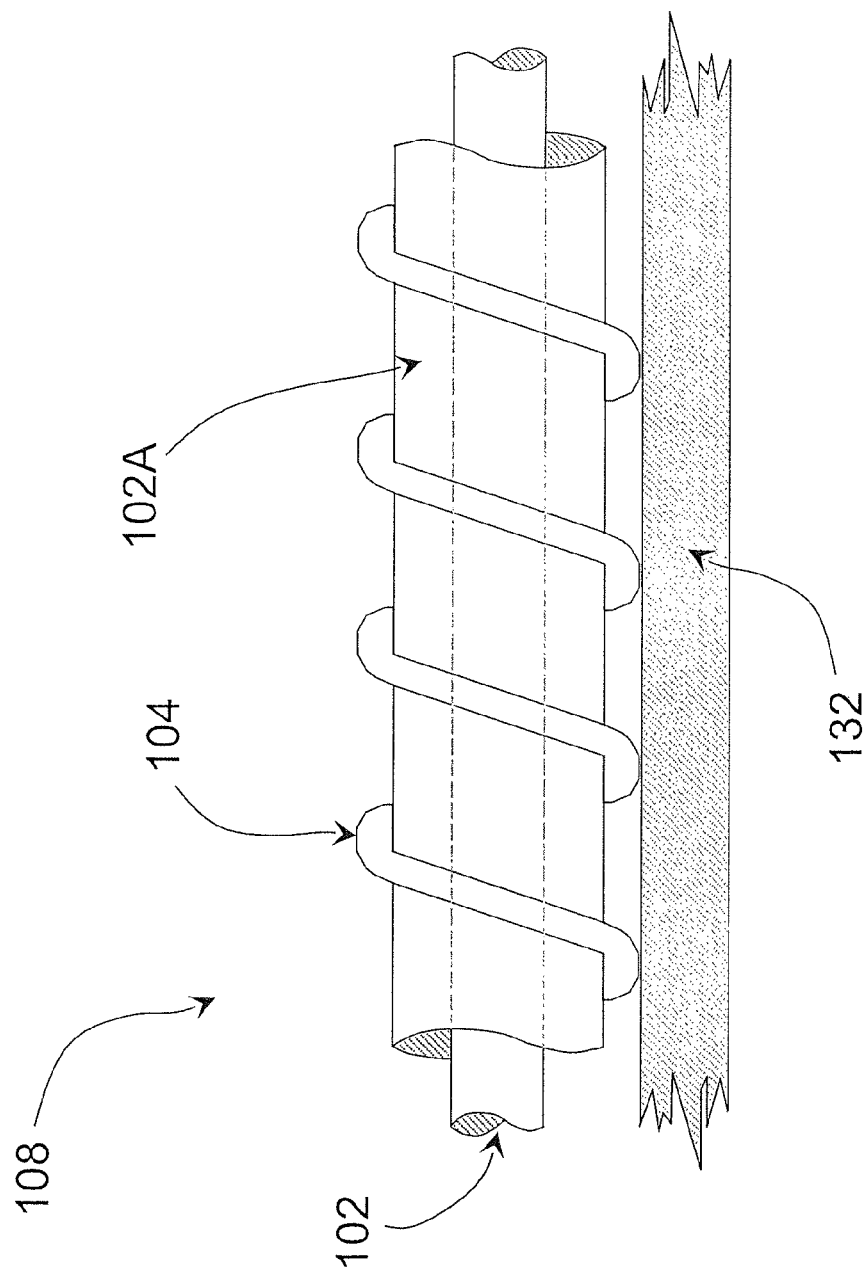

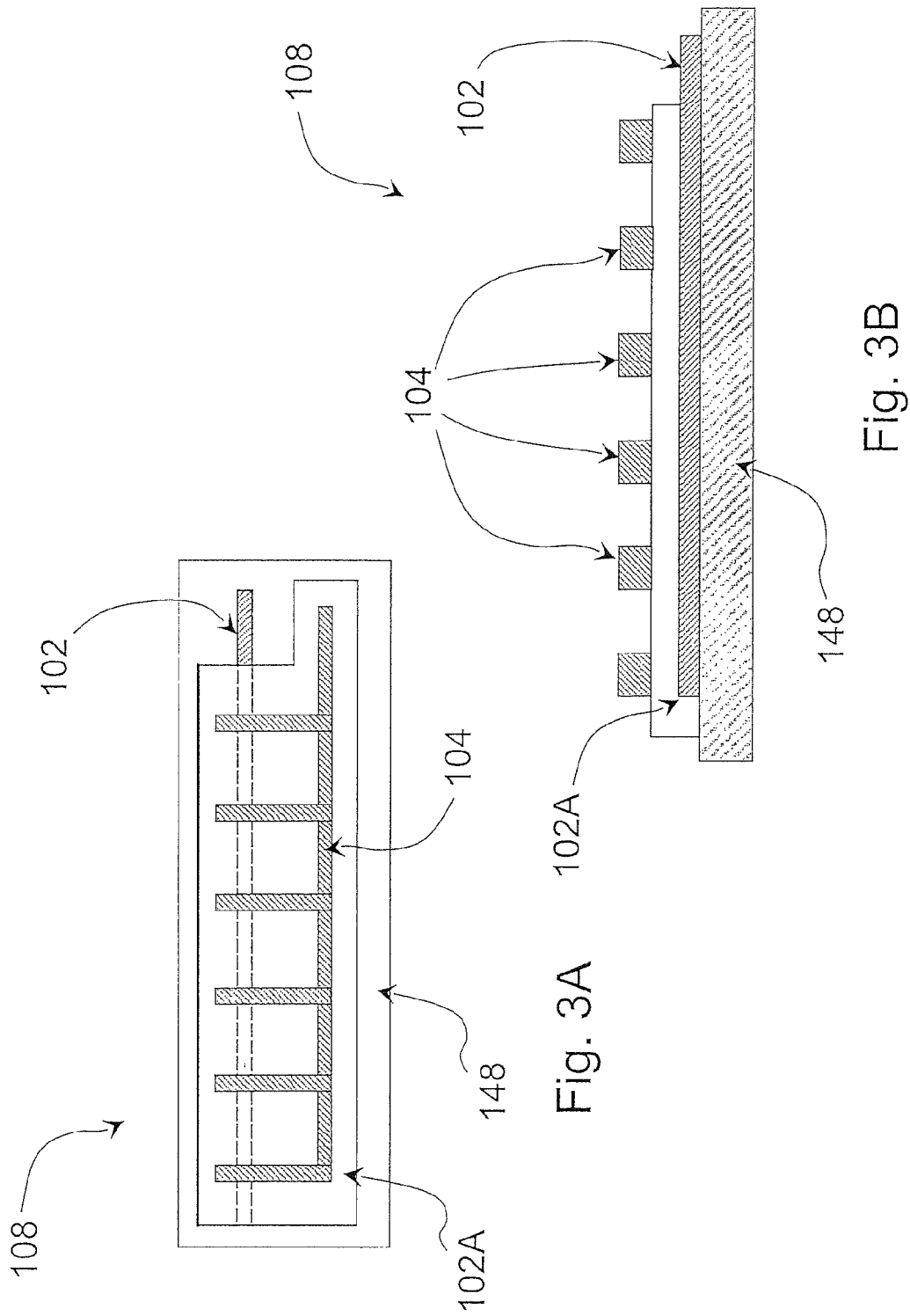

DIELECTRIC BARRIER DISCHARGE IONIZATION SOURCE FOR SPECTROMETRY

This application claims the benefit of U.S. Provisional Application No. 61/908,887, filed Nov. 26, 2013, the contents of which are incorporated herein by reference in their entirety.

BACKGROUND

Ion Mobility Spectroscopy (IMS) is used to determine the composition of sample gases through time-of-flight analysis of their constituent ions. In order to accomplish this, neutral atoms of sample gases are subjected to an ionization process that includes direct bombardment by energetic electrons causing secondary electron liberation from neutral atoms or molecules and creation of primary positive (+) ions; attachment of low energy electrons to neutral atoms or molecules creating (−) ions; chemical reactions and charge exchange between ions and neutral atoms or molecules; attachment of ions to neutral atoms or molecules; and recombination processes between charged particles. After the composition of ions has stabilized, the ions are gated into the drift region of a drift tube at regular intervals using a homogenous electric field. Once inside the drift region, their different mobilities and resultant chemical identities are determined based on their ion charge, ion mass and ion shape.

SUMMARY

An ionization device includes a first electrode comprising a conductive member coated with a dielectric layer. The ionization device also includes a spine extending adjacent to and at least partially along the first electrode. The ionization device further includes a second electrode comprising conductive segments disposed adjacent the first electrode. Each one of the conductive segments contacts the spine at a respective contact location. The dielectric layer of the first electrode separates the conductive member of the first electrode from the spine and the second electrode. The ionization device is configured to create plasma generating locations corresponding to respective crossings of the first electrode and the second electrode.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. The use of the same reference number in different instances in the description and the figures may indicate similar or identical items.

FIG. 2B is a partial cross-sectional end view of the ionization device illustrated in FIG. 2A.

FIG. 2C is a partial cross-sectional end view of an ionization device for an IMS device, such as the IMS device illustrated in FIG. 1, where the ionization device includes a conductive support comprising a nonconductive support material with conductive material applied thereto in accordance with an example embodiment of the present disclosure.

FIG. 2D is a partial cross-sectional end view of an ionization device for an IMS device, such as the IMS device illustrated in FIG. 1, where the ionization device includes multiple dielectric coated electrodes partially surrounding a conductive support in accordance with an example embodiment of the present disclosure.

FIG. 2E is a partial cross-sectional side view of an ionization device for an IMS device, such as the IMS device illustrated in FIG. 1, where the ionization device includes a conductive support positioned outside of a coiled electrode, and where the coiled electrode has external parallel contacts with a conductive surface of the conductive support in accordance with an example embodiment of the present disclosure.

FIG. 3A is a top plan view illustrating an ionization device for an IMS device, such as the IMS device illustrated in FIG. 1, where the ionization device has a planar form in accordance with an example embodiment of the present disclosure.

FIG. 3B is a partial cross-sectional side view of the ionization device illustrated in FIG. 3A.

DETAILED DESCRIPTION

Figure 1:
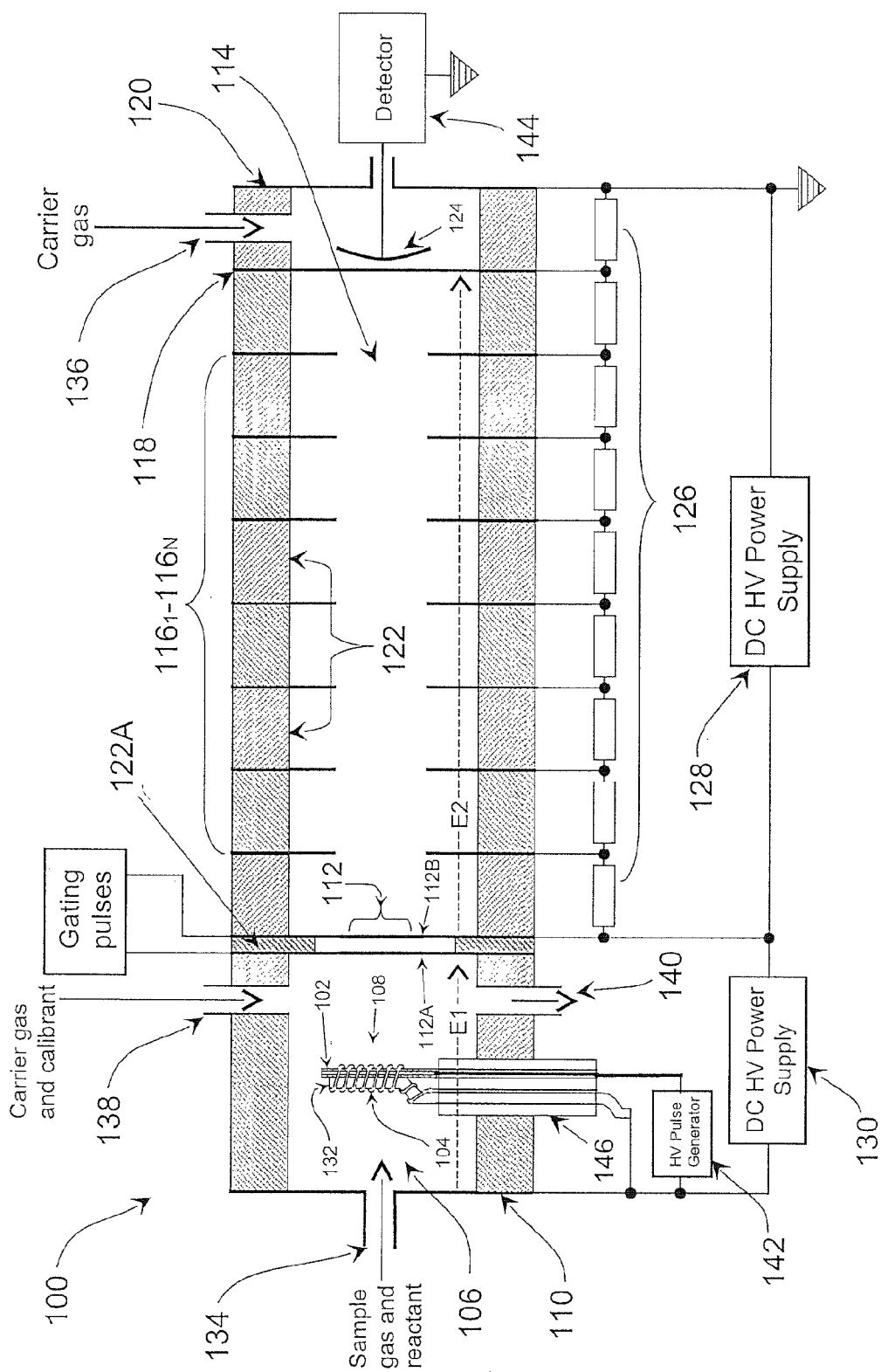
FIG. 1 is a cross-sectional side elevation view of an IMS device including an ionization device in accordance with an example embodiment of the present disclosure.

Primary electrons required for the initial part of an ionization process are typically provided by Radioactive β-particle sources, such as Nickel isotope $^{63}$Ni; thermionic-emission of electrons from heated electrodes, which have a limited life due to evaporation; and electric field emission from sharp points, edges, or fine wires using direct current (DC) or alternating current (AC) corona discharge phenomenon. However, corona discharge techniques generally suffer from poor ignition stability and limited life due to erosion from ion bombardment. Accordingly, devices, systems, and techniques are described that can eliminate radioactive sources, reduce or minimize aging effects, and improve stability in IMS systems. An ionization device is provided that comprises two or more electrodes isolated from one another by a dielectric biased by a time variable voltage. Sample gas and reactant gas are ionized when injected into the vicinity of the of the ionization device. Alternating high voltage excitation is used to generate ionizing plasma via dielectric barrier discharge, which in turn creates ions from both the reactant and sample gases for sample analysis through measurement of their drift movement. The ionization device provides multiple mutual electrode crossings corresponding to multiple simultaneously ignited plasma generating locations, which are energized across a parallel electrical connection. In some embodiments, a first electrode, isolated by a dielectric in the form of a glass-coating (i.e. glass-coated wire), is wrapped together with a metallic supporting rod by a second electrode in the form of a coil of fine wire. At the crossings with the first glass-coated electrode, each individual loop of the second electrode creates two spots of concentrated electric field suitable for plasma ignition. The electrodes can be energized by a series of alternating voltage bursts and biased with respect to a gate electrode such that ions of interest drift toward the gate.

Referring generally to FIGS. 1 through 3C, an ion mobility spectrometer (TMS) device 100 is described. In embodiments of the disclosure, the IMS device 100 is used to ionize gases and/or vapors from samples of interest. For example, plasma is generated by the dielectric barrier discharge between an electrode 102 and an electrode 104 and used to ionize a sample. As described herein, an example IMS device 100 includes an ionization chamber 106 with an ionization device 108. The ionization chamber 106 is formed between an electrode 110 and a gate electrode 112A of an ion gate 112. In this manner, the electrode 110 and the gate electrode 112A define an internal electric field E1. The IMS device 100 also includes a drift channel 114 comprising stacked electrodes $116_1$-$116_N$, where each electrode has an aperture formed therein. The drift channel 114 also includes a grid electrode 118, a ground electrode 120, the gate electrode 112A, and another gate electrode 112B. The electrodes are separated from one another by dielectric spacers 122. In this manner, the drift channel 114 is configured to provide a generally homogeneous internal electric field E2 for time-of-flight analysis of ions collected on a collector electrode 124.

In some embodiments, the drift channel 114 is between about two millimeters (2 mm) and fifty millimeters (50 mm) in diameter, and between about twenty millimeters (20 mm) and two hundred millimeters (200 mm) in length. However, these ranges are provided by way of example only and are not meant to limit the present disclosure. In other embodiments, the drift channel 114 may have a different diameter (e.g., less than two millimeters (2 mm) or greater than fifty millimeters (50 mm)) and/or a different length (e.g., less than twenty millimeters (20 mm) or greater than two hundred millimeters (200 mm)).

A voltage divider comprising a set of serially connected resistors 126 is subjected to voltage supplied by a power source (e.g., a direct current (DC) high voltage (HV) power supply 128). In embodiments of the disclosure, the voltage divider provides the gate electrode 112B, the stacked electrodes $116_1$-$116_N$, the grid electrode 118, and the collector electrode 124 with linearly increasing potentials to furnish homogeneity to the internal electric field E2 of the drift channel 114, which can be on the order of several hundred volts per centimeter (V/cm). In some embodiments, the polarity of the power supply 128 is switchable (e.g., to facilitate analysis of oppositely charged ions).

In comparison to the internal electric field E2 of the drift channel 114, the internal electric field E1 of the ionization chamber 106 is defined by the voltage difference and distance between the electrode 110 and the gate electrode 112A. For example, the electrode 110 and the gate electrode 112A are connected to a power source, such as a DC HV power supply 130. In some embodiments, the internal electric field E1 of the ionization chamber 106 is on the order of between about twenty volts per centimeter (20 V/cm) and five hundred volts per centimeter (500 V/cm). For instance, the internal electric field E1 is on the order of between about fifty volts per centimeter (50 V/cm) and three hundred volts per centimeter (300 V/cm). Further, the internal electric field E1 has the same orientation as the internal electric field E2 and may be smaller or larger than the internal electric field E2 to provide ion extraction. It is also noted that while the power supplies 128 and 130 are shown and described separately, in some embodiments a single power supply is provided in place of the power supplies 128 and 130.

Figure 2A:
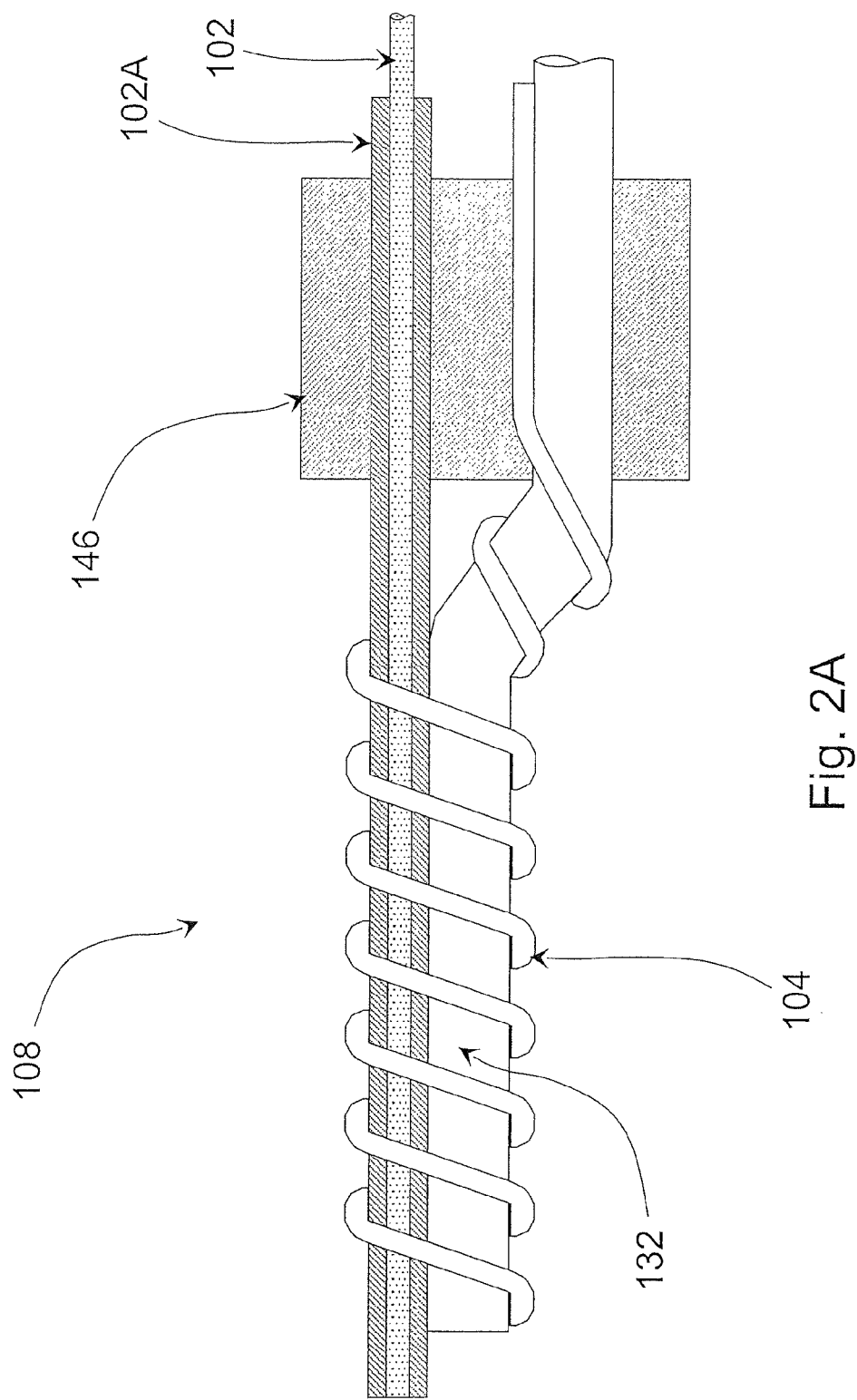
FIG. 2A is a partial cross-sectional side view of an ionization device for an IMS device, such as the IMS device illustrated in FIG. 1, in accordance with an example embodiment of the present disclosure.

Referring now to FIGS. 2A and 2B, ionization device 108 includes electrodes 102 and 104, which are separated from one another by a dielectric layer 102A. In some embodiments, the ionization device 108 extends into the ionization chamber 106 via a conduit 146. The ionization device 108 also includes a conductive, semi-conductive, or non-conductive spine 132 (e.g., a supporting metallic rod or tube) that provides mechanical support to the first electrode 102. In some embodiments, the first electrode 102 is made of a conductive member (e.g., a thin tungsten wire about one-tenth of a millimeter (0.1 mm) in diameter) coated by the dielectric layer 102A (e.g., a thin glass layer several tens of microns thick). The spine 132 extends adjacent to and at least partially along the first electrode 102. In some embodiments, the first electrode 102, isolated by a dielectric later 102A, is in direct physical contact with the spine 132. For example, the first electrode 102 is mechanically connected to the spine 132 by the second electrode 104. In the embodiment shown in FIG. 2E, the spine 132 is positioned outside of the coiled electrode 104, and the coiled electrode 104 has external parallel contacts with the spine 132.

The spine 132 electrically contacts multiple conductive segments (e.g., loops) of the second electrode 104 at respective contact locations. In some embodiments, the second electrode 104 is formed from a thin wire several tens of microns in diameter encircling (e.g., wrapped around) the first electrode 102 (and possibly the spine 132). For example, the second electrode 104 comprises multiple loops with a pitch between successive turns of between at least approximately twenty-five one thousandths of a millimeter (0.025 mm) and fifty millimeters (50 mm). In embodiments of the disclosure, the second electrode 104 comprises one or more metals and/or alloys with low chemical reactivity, low sputtering rate, and/or low work function (e.g. tungsten (W), titanium (Ti), tantalum (Ta), rhodium (Rh), nickel carbide ($Ni_3C$), and so forth).

Ionization of analyte gasses or vapors for analysis proceeds in several steps. Ionization starts with a short burst of variable voltage of sinusoidal, triangular, rectangular or another arbitrary form with regular or arbitrary time resolved repetition, applied to electrodes 102 and 104 of the ionization device 108. In some embodiments, the short voltage bursts have amplitudes between about five hundred volts (500V) and ten thousand volts (10,000V) (e.g., between about one thousand volts (1,000V) and five thousand volts (5,000V)). Further, the applied voltage can alternate with a frequency below about ten megahertz (10 MHz) (e.g., between about ten kilohertz (10 kHz) and five megahertz (5 MHz)). The applied voltage creates a strong variable electric field in areas proximate to crossings of the electrodes 102 and 104. When the variable electric field exceeds a critical value, dielectric barrier discharge is ignited creating a corona. A corona is created when randomly present electrons are accelerated between subsequent collisions to energies larger than the ionization energy of atoms and molecules of surrounding gasses and/or vapors. During discharge, the dielectric barrier is continuously charged, causing the electric field to diminish, which in turn results in a brief termination of the ionization process. In the presence of the corona, primary positive (+) ions and primary negative (−) ions are generated by electron bombardment or attachment, respectively.

Analyte gasses and/or vapors are introduced into the vicinity of the ionization device 108 inside the ionization chamber 106 through an inlet 134, which can be located at an end of the IMS device 100. Carrier gas (e.g., dry air) is supplied through another inlet 136 into the ion detection end of the drift channel 114. In some embodiments, to increase the yield of ionized atoms and/or molecules from analytes, a reactant gas of higher electron or proton affinity with respect to the primary ions is injected in the form of a mixture with carrier gas into the ionization chamber 106 (e.g., through the inlet 134 and/or another inlet 138). In some embodiments, an outlet 140 is also provided in the ionization chamber 106.

Ions from an ion cloud created by the electron bombardment, chemical ionization, attachment processes, and so forth, drift with respect to their polarity, toward the electrode 110 or the gate electrode 112A. In embodiments of the disclosure, the ion gate 112 separating the ionization chamber 106 from the drift channel 114 comprises two closely positioned grid-like gate electrodes 112A and 112E isolated from each other by a thin dielectric 122A (e.g., with a thickness on the order of several tens of microns). In a "closed" state, voltage applied to the gate electrodes 112A and 112B creates an electric field between the electrodes with a radial component of opposite orientation with respect to both the internal electric field E2 of the drift channel 114 and the electric field E1 of the ionization chamber 106. In some embodiments, the voltage difference between the gate electrodes 112A and 112B is on the order of several tens of volts depending upon their geometries.

The ion gate 112 is "opened" for a short time (e.g., between about fifty microseconds (50 µsec) and three hundred microseconds (300 µsec)) by a pulse having a desired polarity. In some embodiments, the pulse is delayed with respect to a plasma trigger to allow for a desired amount of analyte ions to reach the region of the ionization chamber 106 proximate to the ion gate 112. The plasma trigger can be supplied by, for example, an HV pulse generator 142. In some embodiments, the pulse delay is between about zero milliseconds (0 msec) and ten milliseconds (10 msec) (e.g., between about one-half millisecond (0.5 msec) and three milliseconds (3 msec)) depending on the dimensions of the ionization chamber 106, reaction rates of generated ions, the electric field E1, and ion mobility. Ions are identified by analyzing their time-of-flight from the moment the ion gate 112 opens to the time of their arrival at the collector electrode 124. For example, a detector 144 is used to identify one or more ions based upon their respective times-of-flight.

Referring now to FIG. 2C, in some embodiments, the spine 132 comprises nonconductive support material (e.g., a supporting rod or tube) with conductive material 132A applied thereto. For example, a strip of conductive material 132A is disposed between nonconductive support material of the spine 132 and the first electrode 102. In other embodiments, the spine 132 comprises a nonconductive support material with a metalized (or partially metalized) surface.

With reference to FIG. 2D, in some embodiments, plasma generating locations are provided using multiple dielectric coated electrodes 102. In some embodiments, the spine 132 can be partially surrounded by the electrodes 102. In this configuration, the second electrode 104 encircles multiple first electrodes 102 (and possibly the spine 132).

Figure 3C:
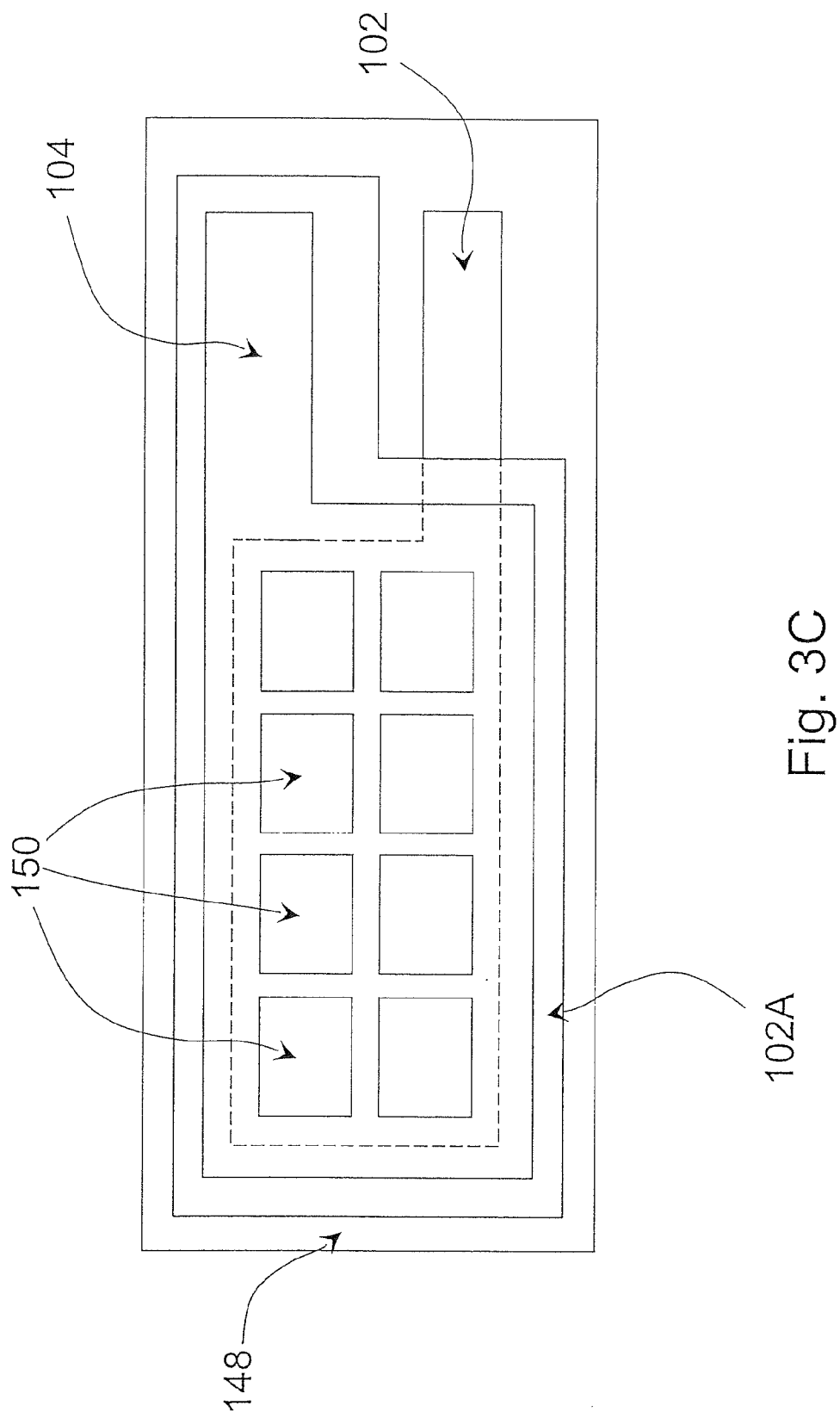
FIG. 3C is a top plan view illustrating an ionization device for an IMS device, such as the IMS device illustrated in FIG. 1, where the ionization device has a planar form with multiple apertures defined by a branched planar electrode in accordance with an example embodiment of the present disclosure.

Referring now to FIGS. 3A through 3C, the ionization device 108 can also be formed using a planar configuration with planar electrodes. For example, as shown in FIGS. 3A and 3B, a conductive member comprising a first planar electrode is positioned on a substrate 148 and sealed by the dielectric layer 102A. In this embodiment, the second electrode 104 comprises a second branched planar electrode with multiple crossings of the first electrode 102, where locally enhanced electric fields simultaneously trigger the dielectric barrier discharges. With reference to FIG. 3C, the second planar electrode 104 defines a single aperture 150 or a matrix of apertures 150, in which the plasma is also generated simultaneously. It is noted that in these embodiments, the planar ionization components can be produced by lamination, vacuum deposition techniques, and so forth.

Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claims.

What is claimed is:

1. An ionization device comprising:
    a first electrode comprising a conductive member coated with a dielectric layer;
    a spine extending adjacent to and at least partially along the first electrode; and a second electrode comprising a plurality of conductive segments disposed adjacent the first electrode, each one of the plurality of conductive segments contacting the spine at a respective contact location, the dielectric layer of the first electrode separating the conductive member of the first electrode from the spine and the second electrode, and the ionization device configured to create a plurality of plasma generating locations corresponding to respective crossings of the first electrode and the second electrode.

2. The ionization device as recited in claim 1, wherein the second electrode comprises a plurality of loops encircling the first electrode.

3. The ionization device as recited in claim 1, wherein the second electrode encircles both the first electrode and the spine.

4. The ionization device as recited in claim 2, wherein a pitch between successive turns of the plurality of loops of the second electrode is between at least approximately twenty-five one thousandths of a millimeter (0.025 mm) and fifty millimeters (50 mm).

5. The ionization device as recited in claim 1, wherein the spine comprises a nonconductive support material with conductive material applied thereto.

6. The ionization device as recited in claim 1 wherein the first electrode comprises a plurality of dielectric coated electrodes.

7. The ionization device as recited in claim 6, wherein the second electrode comprises a plurality of loops encircling the first electrode and the spine.

8. An ion mobility spectrometer (IMS) device comprising:
    an ionization chamber for ionizing at least one of a gas or vapor of interest;
    an ionization device disposed in the ionization chamber, the ionization device comprising a first electrode comprising a conductive member coated with a dielectric layer; a spine extending adjacent to and at least partially along the first electrode; and a second electrode comprising a plurality of conductive segments disposed adjacent the first electrode, each one of the plurality of conductive segments contacting the spine at a respective contact location, the dielectric layer of the first electrode separating the conductive member of the first electrode from the spine and the second electrode, and the ionization device configured to create a plurality of plasma generating locations corresponding to respective crossings of the first electrode and the second electrode;

a drift channel in fluid communication with the ionization chamber;

a gate disposed between the ionization chamber and the drift channel for selectively providing access from the ionization chamber to the drift channel; and a collector electrode disposed at an end of the drift channel opposite the gate, the collector electrode for collecting ions from the at least one of the gas or vapor of interest.

9. The IMS device as recited in claim 8, wherein the second electrode comprises a plurality of loops encircling the first electrode.

10. The IMS device as recited in claim 8, wherein the second electrode encircles both the first electrode and the spine.

11. The IMS device as recited in claim 9, wherein a pitch between successive turns of the plurality of loops of the second electrode is between at least approximately twenty-five one thousandths of a millimeter (0.025 mm) and fifty millimeters (50 mm).

12. The IMS device as recited in claim 8, wherein the spine comprises a nonconductive support material with conductive material applied thereto.

13. The IMS device as recited in claim 8, wherein the first electrode comprises a plurality of dielectric coated electrodes.

14. The IMS device as recited in claim 13, wherein the second electrode comprises a plurality of loops encircling the first electrode and the spine.

15. An ionization device comprising:

a first electrode comprising a conductive wire coated with a dielectric layer;

a conductive support extending adjacent to and at least partially along the first electrode; and a second electrode comprising a plurality of conductive loops encircling the first electrode, each one of the plurality of conductive loops contacting the conductive support at a respective contact location, the dielectric layer of the first electrode separating the conductive wire of the first electrode from the conductive support and the second electrode, and the ionization device configured to create a plurality of plasma generating locations corresponding to respective crossings of the first electrode and the second electrode.

16. The ionization device as recited in claim 15, wherein the second electrode encircles both the first electrode and the conductive support.

17. The ionization device as recited in claim 15, wherein a pitch between successive turns of the plurality of loops of the second electrode is between at least approximately twenty-five one thousandths of a millimeter (0.025 mm) and fifty millimeters (50 mm).

18. The ionization device as recited in claim 15, wherein the conductive support comprises a nonconductive support material with conductive material applied thereto.

19. The ionization device as recited in claim 15, wherein the first electrode comprises a plurality of dielectric coated electrodes.

20. The ionization device as recited in claim 15, wherein the second electrode comprises a plurality of loops encircling the first electrode and the conductive support.

* * * * *